(12) United States Patent (10) Patent No.: US 9,713,493 B2
Waaler et al. (45) Date of Patent: Jul. 25, 2017

(54) METHOD OF SWITCHING ENERGY MODALITY ON A CORDLESS RF DEVICE

(75) Inventors: Luke Waaler, Longmont, CO (US); William E. Robinson, Boulder, CO (US); Jason L. Craig, Loveland, CO (US); Diana Gunnarson, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1094 days.

(21) Appl. No.: 13/460,455

(22) Filed: Apr. 30, 2012

(65) Prior Publication Data

US 2013/0289561 A1 Oct. 31, 2013

(51) Int. Cl.
A61B 18/12 (2006.01)
A61B 18/14 (2006.01)
A61B 18/18 (2006.01)
A61B 18/00 (2006.01)

(52) U.S. Cl.
CPC ...... *A61B 18/1477* (2013.01); *A61B 18/1206* (2013.01); *A61B 18/1442* (2013.01); *A61B 18/1815* (2013.01); *A61B 2018/0063* (2013.01)

(58) Field of Classification Search
CPC ............ A61B 18/1206; A61B 18/1442; A61B 18/1477; A61B 18/1815; A61B 2018/0063
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Amanda Patton

(57) ABSTRACT

The present disclosure is directed to an electrosurgical instrument having a housing that includes a generator configured to output electrosurgical energy and a controller configured to control the output of the generator. The instrument also includes a switch coupled to the controller and configured to provide a signal to the controller to select the energy modality of the electrosurgical energy. An indicator is also included to provide an indication of the selected energy modality.

11 Claims, 14 Drawing Sheets

(56) References Cited

U.S. PATENT DOCUMENTS

| | | |
|---|---|---|
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,537,272 B2 | 3/2003 | Christopherson et al. |
| 6,652,514 B2 | 11/2003 | Ellman et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,156,842 B2 | 1/2007 | Sartor et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,957,798 B2 * | 6/2011 | Pearce ............... A61N 1/39 607/5 |
| D649,249 S | 11/2011 | Guerra |
| D649,643 S | 11/2011 | Allen, IV et al. |
| 8,048,069 B2 * | 11/2011 | Skwarek et al. ......... 606/38 |
| 2009/0248007 A1 | 10/2009 | Falkenstein et al. |
| 2011/0172659 A1 * | 7/2011 | Brannan ............... 606/42 |
| 2012/0245576 A1 * | 9/2012 | Epstein et al. ......... 606/33 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.

(56) References Cited

OTHER PUBLICATIONS

U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.

(56) References Cited

OTHER PUBLICATIONS

"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.

(56) References Cited

OTHER PUBLICATIONS

Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

METHOD OF SWITCHING ENERGY MODALITY ON A CORDLESS RF DEVICE

BACKGROUND

1. Technical Field

The present disclosure relates to electrosurgical instruments used for open and endoscopic surgical procedures for sealing or fusing tissue. More particularly, the present disclosure relates to systems and methods for switching energy modalities in a cordless electrosurgical device.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgical instruments have become widely used by surgeons in recent years. By and large, most electrosurgical instruments are hand-held instruments, e.g., electrosurgical pencils, electrosurgical forceps, endoscopic instruments such as monopolar forceps, bipolar forceps or a combination monopolar/bipolar forceps, ultrasonic hand tools, microwave probes. Such electrosurgical instruments are electrically coupled to an external electrosurgical generator. The external electrosurgical generator includes a number of switches, knobs, buttons and/or screens to control the output of the electrosurgical generator. Some electrosurgical instruments are portable and include a generator integrated therein.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As shown in the drawings and described throughout the following description, as is traditional when referring to relative positioning on a surgical instrument, the term "proximal" refers to the end of the apparatus that is closer to the user or generator and the term "distal" refers to the end of the apparatus that is farther away from the user or generator. The term "clinician" refers to any medical professional (i.e., doctor, surgeon, nurse, or the like) performing a medical procedure involving the use of aspects of the present disclosure described herein.

Electromagnetic (EM) energy is generally classified by increasing frequency or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves. As used herein, the term "ultrasound" generally refers to cyclic sound pressure with a frequency greater than the upper limit of human hearing. The terms "tissue" and "vessel" may be used interchangeably since it is believed that the present disclosure may be employed to seal and cut tissue or seal and cut vessels utilizing the same principles described herein.

The phrase "electrosurgical instrument" may refer to any instrument configured to output electrosurgical energy such as electrosurgical pencils, electrosurgical forceps, endoscopic instruments such as monopolar forceps, bipolar forceps or a combination monopolar/bipolar forceps, ultrasonic hand tools, microwave probes. The phrase "electrosurgical energy" may refer to energy used to perform a surgical procedure such as electromagnetic energy or acoustic energy. The phrase "end effector" may refer to any device capable of emitting electromagnetic energy or acoustic energy to treat tissue within the vicinity of the end effector. Types of end effector may include antennas, ultrasonic transducers, electrodes, jaw members, probes, acoustic waveguides, combinations thereof or the like.

The term "generator" may refer to a device capable of providing electrosurgical energy. Such device may include a power source and electrical components (analog and/or digital components) capable of modifying the energy outputted by the power source to output energy having a desired energy modality. The phrase "energy modality" may refer to the characteristics of the outputted electrosurgical energy. Such characteristics may include an energy mode, which includes the type of energy (e.g., RF, microwave, ultrasound, etc.) and/or waveform (e.g., sine wave, square wave, triangle wave, sawtooth wave, composite waves, etc.), and/or energy level.

The term "switch" may refer to a device for making, breaking or changing the connections in an electrical circuit. Switches used herein may include multi-positional switches, digital switches and/or analog switches that may be disposable or reposable.

The term "indicator" may refer to one or more audio or visual devices that provide information to a user or any other person in the vicinity of the indicator. Example of indicators include, but are not limited to, speakers, light emitted diodes, neon lamps, video displays, printed markers, etc.

The electrosurgical instruments herein may utilize one or more sensors configured to detect one or more properties of tissue and/or the ambient environment. Such properties include, but are not limited to: tissue impedance, tissue type, tissue clarity, tissue compliance, temperature of the tissue or jaw members, water content in tissue, jaw opening angle, water motility in tissue, energy delivery, and jaw closure pressure.

The electrosurgical instruments used herein may also utilize a controller to receive various inputs from a number of switches and or sensors and control the energy modality of the energy outputted by the electrosurgical instrument. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like.

Any of the herein described methods, programs, algorithms or codes may be converted to a programming language or computer program. A "Programming Language" and "Computer Program" is any-language used to specify instructions to a computer, and includes (but is not limited to) these languages and their derivatives: Assembler, Basic, Batch files, BCPL, C, C+, C++, Delphi, Fortran, lava, JavaScript, Machine code, operating system command languages, Pascal, Pearl, PU1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus reference to a program, where the programming language could exist in more than one state (such as source, compiled, object, or linked) is a reference to any and all states. The definition also encompasses the actual instructions and the intent of those instructions.

Any of the herein described methods, programs, algorithms or codes may be contained on one or more machine-readable media or memory. The term "memory" may include a mechanism that provides (i.e., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In an aspect of the present disclosure, an electrosurgical instrument is provided. The electrosurgical instrument includes a housing having a generator configured to output electrosurgical energy and a controller configured to control the output of the generator. The electrosurgical instrument also includes a switch coupled to the controller and configured to provide a signal to the controller to select the energy modality of the electrosurgical energy. An indicator is also included in the electrosurgical instrument to provide an indication of the selected energy modality.

The energy modality may include an energy level and the indicator provides an indication of the energy level or the energy modality may include an energy mode and the indicator provides an indication of the energy mode. Alternatively, the energy modality may include an energy level and an energy mode and the indicator provides an indication of the energy level and the energy mode. The indicator may be an audio device or a visual device such as a light emitting diode.

The housing may include a recess defined therein and the switch is disposed in the recess. The housing may include a rib surrounding the switch. The housing may also include a cover disposed over the switch that is configured to be opened in order to operate the switch.

The electrosurgical instrument may include a safety configured to prevent adjustment of the switch, wherein the switch is only operable when the safety is de-activated.

The switch may be a multi-position switch, a rotary switch that may include a potentiometer. The switch may be integrated into the housing or removable coupled from the housing.

The instrument may also include a memory having a plurality of energy modalities stored thereon.

In another aspect of the present disclosure, an electrosurgical instrument may be provided that includes a housing having a generator configured to output electrosurgical energy and a controller configured to control the output of the generator. The electrosurgical instrument also includes a touch screen coupled to the controller and configured to provide a signal to the controller to select the energy modality of the electrosurgical energy.

The energy modality may include an energy level and the touch screen provides an indication of the energy level or the energy modality may include an energy mode and the touch screen provides an indication of the energy mode. Alternatively, the energy modality may include an energy level and an energy mode and the touch screen provides an indication of the energy level and the energy mode.

The touch screen is configured to receive clinician identification information and/or patient identification information. The touch screen may be configured to display information corresponding to the clinician identification information and/or the patient identification information.

The touch screen may also be configured to receive biometric information. The electrosurgical instrument may also include a memory having biometric information stored thereon and the controller compares the received biometric information to the biometric information stored in a memory.

The electrosurgical instrument may also include a memory having a plurality of energy modalities stored thereon.

In yet another aspect of the present disclosure, an electrosurgical instrument may be provided having a housing including a generator configured to output electrosurgical energy, an end effector coupled to the generator and configured to output electrosurgical energy to tissue, and a control unit coupled to the housing. The control unit includes a controller configured to control the output of the generator and a touch screen coupled to the controller and configured to provide a signal to the controller to select the energy modality of the electrosurgical energy.

The control unit may be removably coupled to the housing.

The energy modality may include an energy level and the touch screen provides an indication of the energy level or the energy modality may include an energy mode and the touch screen provides an indication of the energy mode. Alternatively, the energy modality may include an energy level and an energy mode and the touch screen provides an indication of the energy level and the energy mode.

The touch screen may also be configured to receive biometric information. The electrosurgical instrument may also include a memory having biometric information stored thereon and the controller compares the received biometric information to the biometric information stored in a memory.

The electrosurgical instrument may also include a memory having a plurality of energy modalities stored thereon.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 2A-2I depict various electrosurgical instruments according to embodiments of the present disclosure;

DETAILED DESCRIPTION

Figure 1:
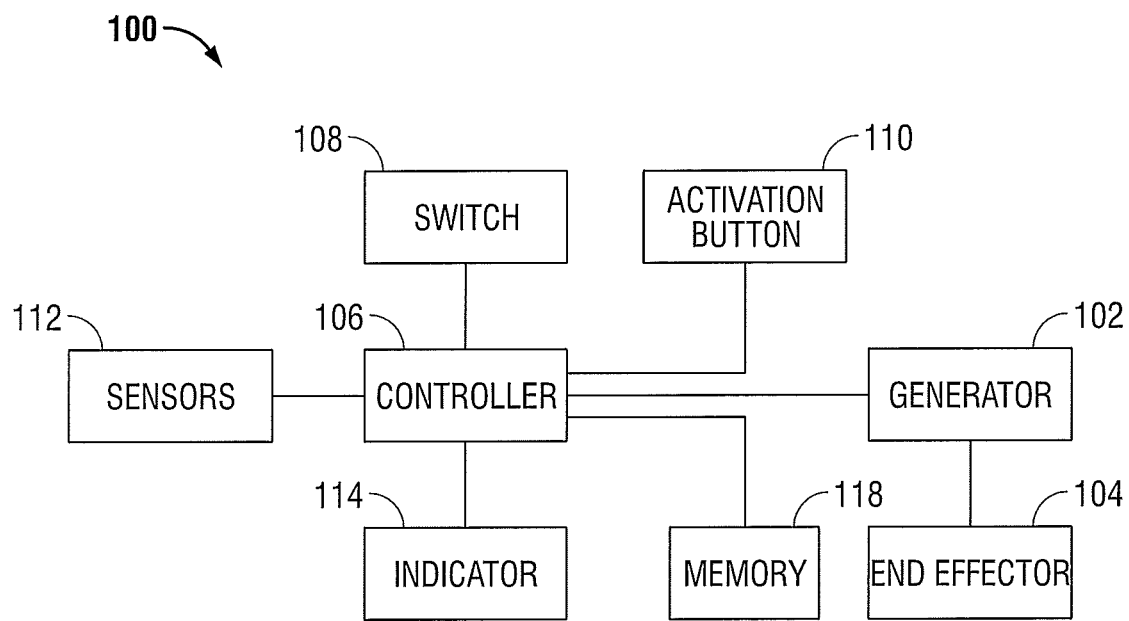
FIG. 1 is a system block diagram of an electrosurgical instrument.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure is directed to an electrosurgical instrument that allows a user to change an energy level in a sterile environment. The electrosurgical instrument includes a switch disposed on the housing to control the energy level. The switch may be disposed on the housing for a one handed or two handed operation. Visual or audible indicators may be provided to indicate the energy level. Additionally, physical characteristics, as will be described below, may be integrated with the switch to minimize inadvertent activation of the switch.

Turning to FIG. 1, a system block diagram of an electrosurgical instrument is shown generally as 100. Instrument 100 includes a generator 102 configured to output electrosurgical energy to end effector 104. End effector 104 outputs the electrosurgical energy to tissue within the vicinity of end effector 104. Instrument 100 also includes a controller 106 that is configured to receive various inputs and output a control signal to generator 102 to control the output of generator 102. Controller 106 may receive inputs from a switch 108 that controls the energy modality of the electrosurgical energy, an activation button 110 that controls application of the electrosurgical energy, and/or sensors 112. Controller 106 is coupled to a memory 118 that has programs and/or algorithms used to control the output of the electrosurgical instrument 100 (e.g., open loop or closed loop feedback programs). Memory 118 may also store a number of programs for controlling the energy modality of the electrosurgical energy. Memory 118 may be a separate component or integrated into controller 106. Controller 106 also controls indicator 114 to output an audible or visual indication upon activation of the electrosurgical instrument 100 or upon a change of energy modality by switch 108.

FIGS. 2A-2I depict various electrosurgical instruments in accordance with various embodiments of the present disclosure. The electrosurgical instruments depicted in FIGS. 2A-2I include a housing 150 that includes generator 102, controller 106, switch 108, and activation button 110. Housing 150 may also include one or more sensors 112. Switch 108 may be permanently fixed to housing 150 or removably coupled to housing 150. Switch 108 may also be reposable or disposable. The switches may also be ergonomically dimensioned and/or disposed on the electrosurgical instrument.

Figure 2A:
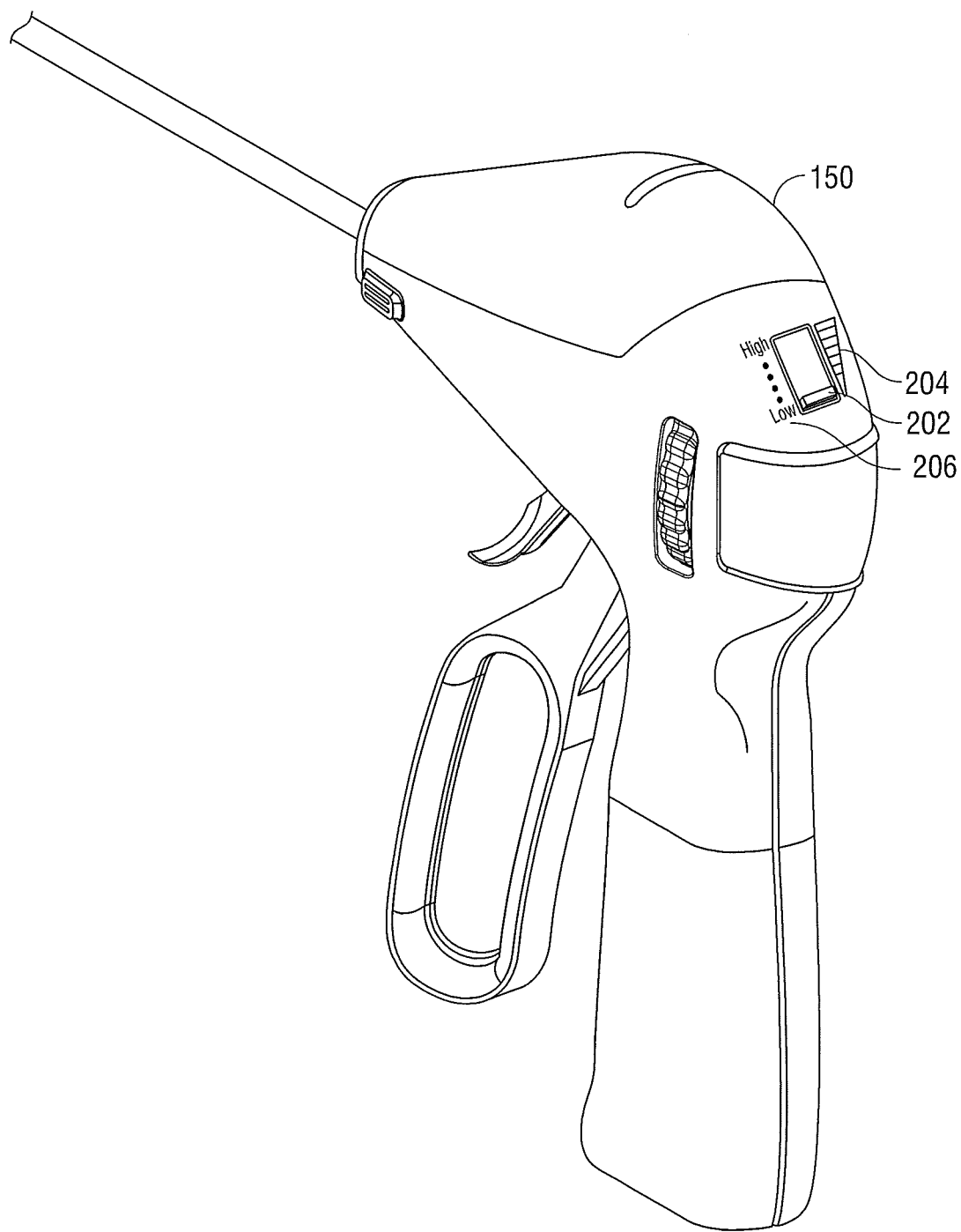

Turning to FIG. 2A, housing 150 includes a multi-position switch 202 that is operated by the clinician to adjust the output of the energy level. Housing 150 may also include one or more indicators that provide the clinician with information regarding the energy level associated with the position of the switch. For instance, indicator 204 may be provided with numerous bars of varying length to indicate the energy level. Alternatively, indicator 206 may be provided text indicating "HIGH" and "LOW" to inform a clinician of which way the switch should be moved to increase or decrease the energy level.

Figure 2B:
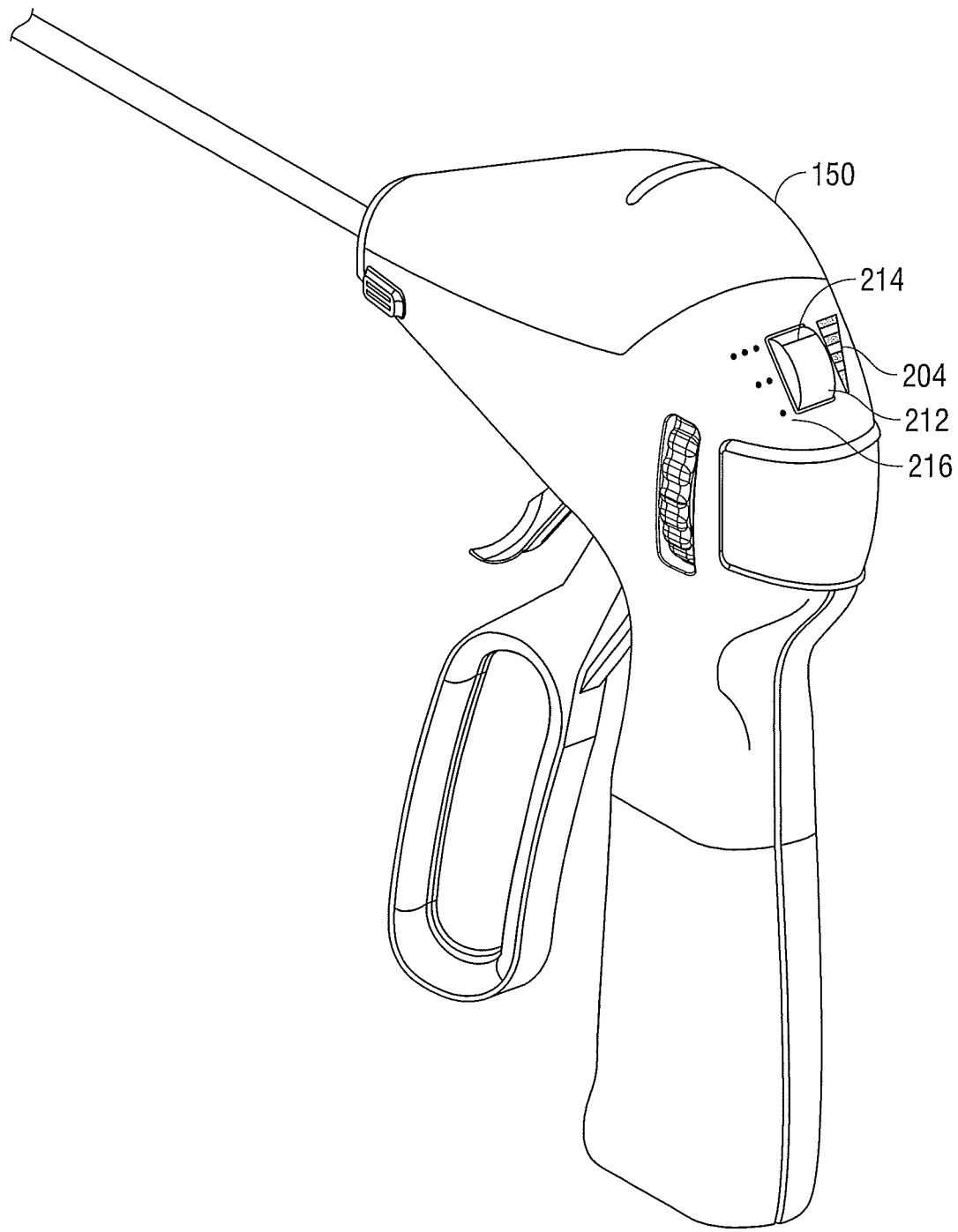

FIG. 2B depicts a housing 150 having a switch 212. Switch 212 may be an analog switch (e.g., a potentiometer) that allows a user to adjust the energy level in small increments to finely tune the energy output. Switch 212 may include an indicator 214 such as a line or an arrow to indicate the energy level being outputted. Alternatively, an indicator 216 may be provided to indicate an energy level being outputting by the electrosurgical instrument. As shown in FIG. 2B, indicator 216 has series of dots that indicate the energy level where an increase in the number of dots indicates an increase in the energy level.

Figure 2C:
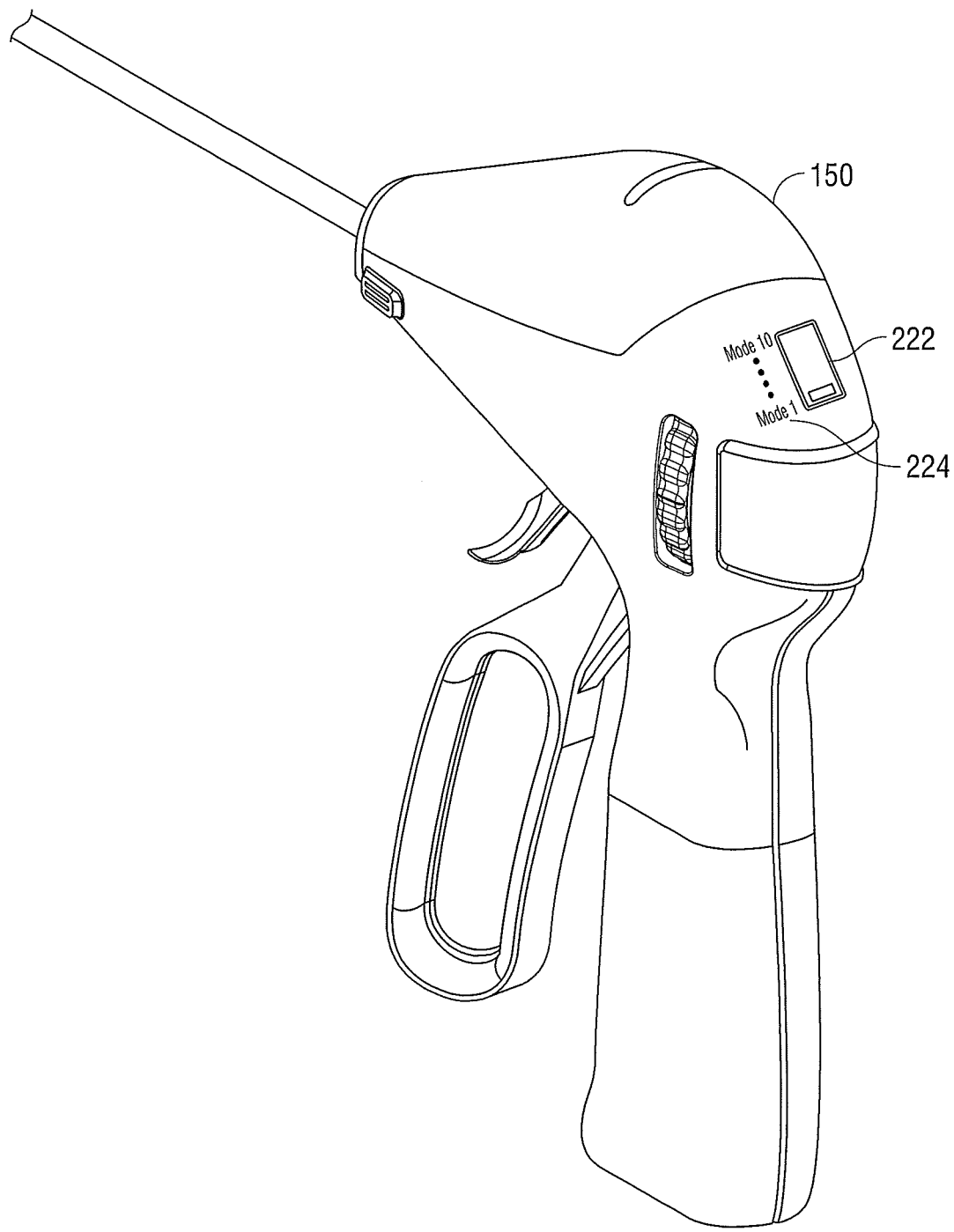
Figure 2D:
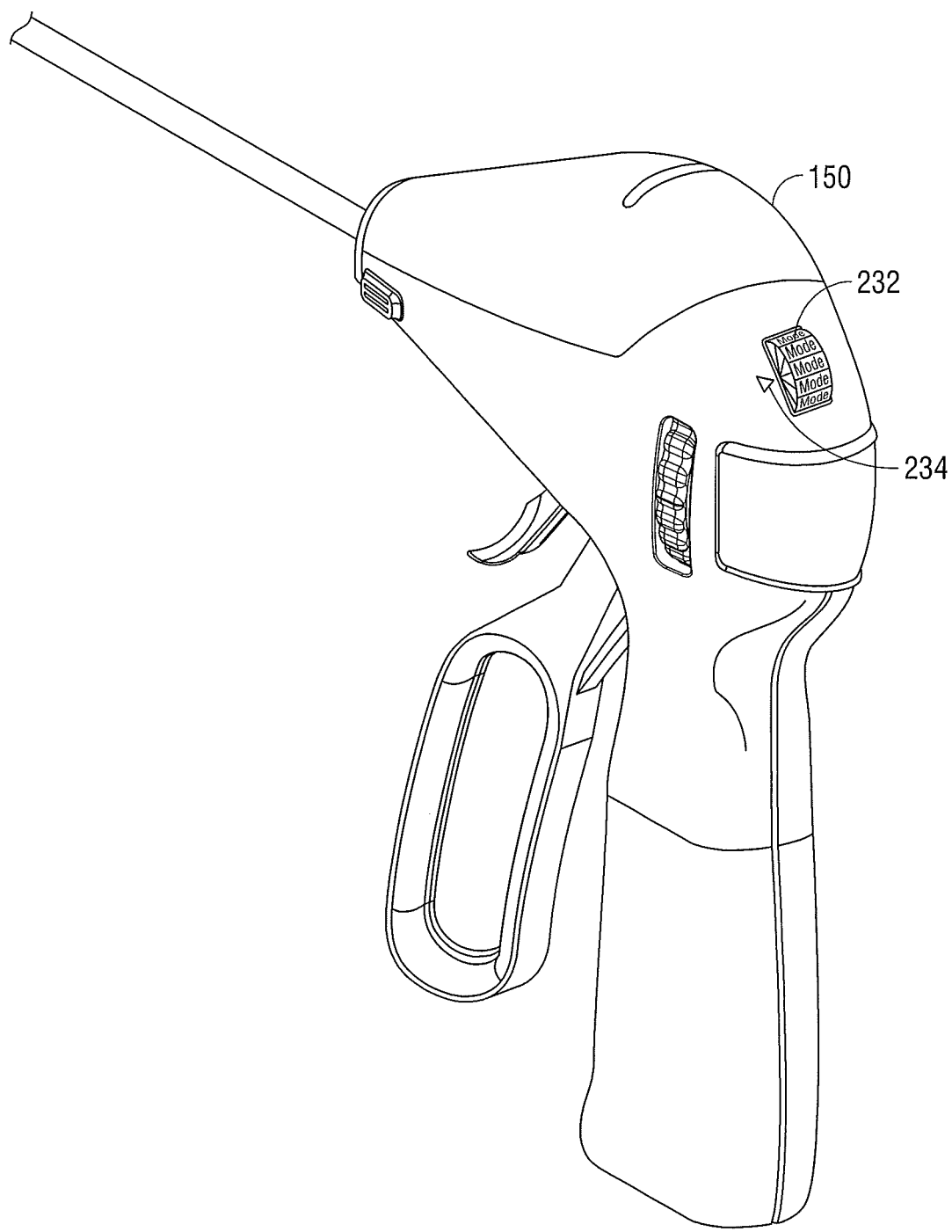

FIG. 2C depicts a housing 150 having a multi-position switch 222 used to control the energy mode of the electrosurgical energy outputted from generator 102. When switch 222 is moved from a first position to a second position, controller 106 determines which energy modality has been selected by a user. Controller 106 then controls generator 102 to output electrosurgical energy having the energy modality selected by the clinician. An indicator 224 is provided to inform the user of which energy modality corresponds to the position of switch 222. Alternatively, as shown in FIG. 2D, a rotary switch 232 may be provided having the modes printed thereon. An arrow 234 is printed next to rotary switch 232 to indicate which energy modality is being selected by the switch.

Any of the switches described above in FIGS. 2A-2D can be used to select a combination of an energy level and an energy mode. The indicators described above can be used to indicate the selected energy level and energy mode. Such indicators may be printed on the electrosurgical instrument or may be a device that emits light (e.g., LEDs).

Figure 2E:
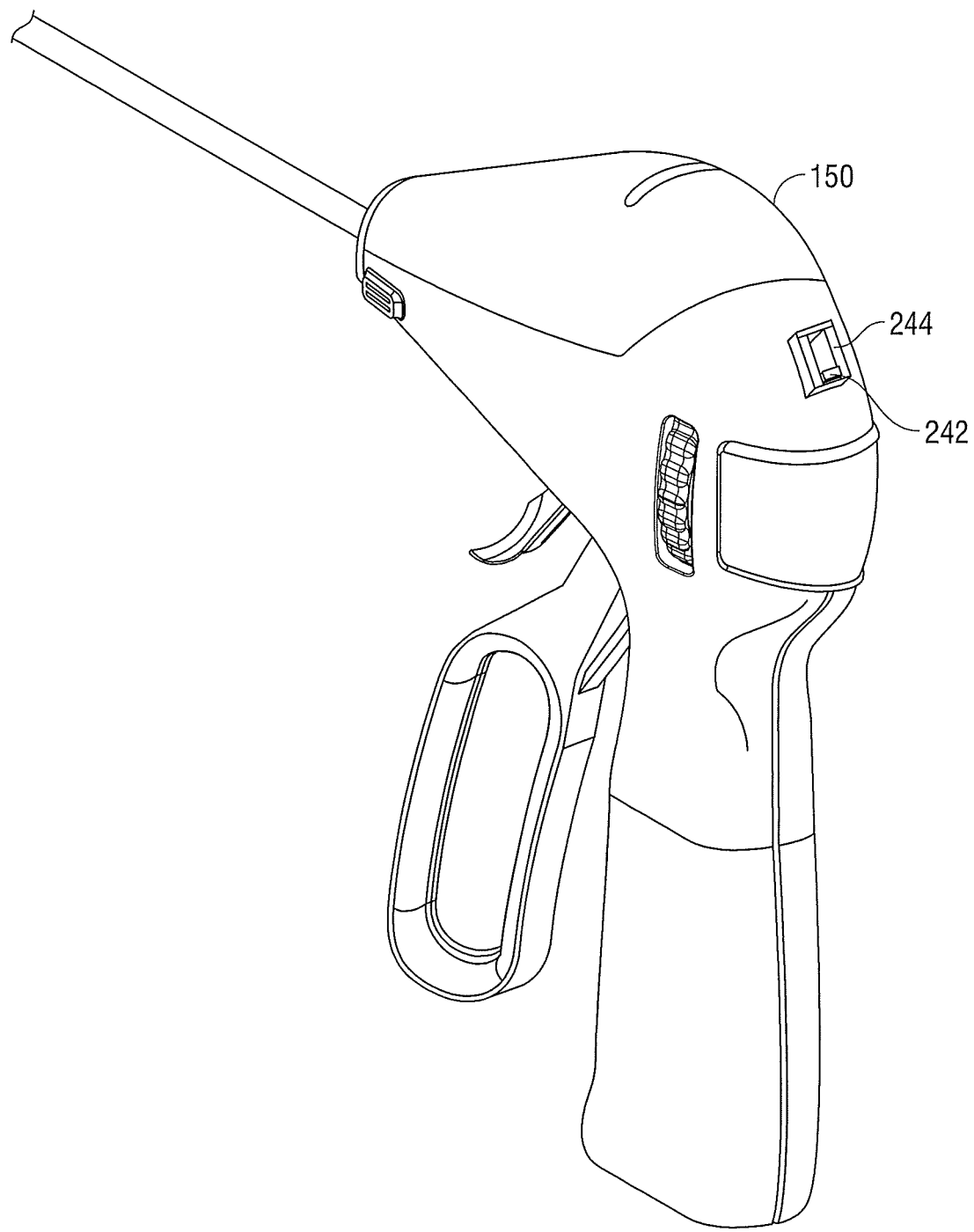

In order to prevent a clinician from accidentally changing the intensity level or energy modality by inadvertently moving the switches described above in FIGS. 2A-2D, one or more safety devices and/or methods may be provided as shown in FIGS. 2E-2H. The safety devices and/or methods shown in FIGS. 2E-H may be combined with any of the switches described above with regard to FIGS. 2A-2D. For instance, as shown in FIG. 2E, a rib 244 is provided surrounding the outer edges of switch 242. Although FIG. 2E shows rib 244 surrounding the entire switch 242, rib 244 may be disposed along one edge, two edges, or three edges of the switch 242. Alternatively, rib 244 may be constructed to conform to any size or shape corresponding to the switch 242 being used. By placing rib 244 around switch 242, a clinician is prevented from inadvertently adjusting the energy modality of the electrosurgical energy.

Figure 2F:
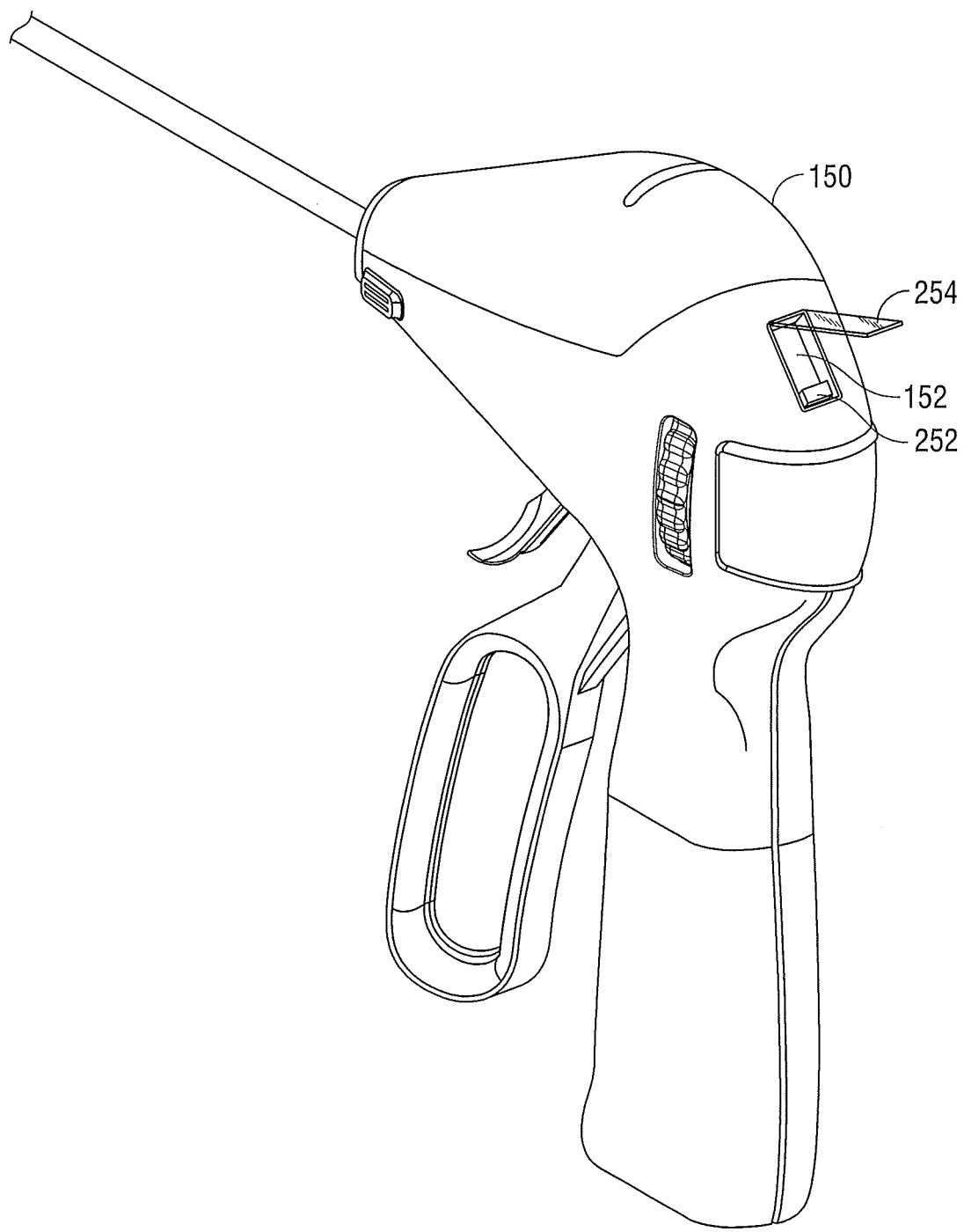

FIG. 2F depicts another safety device according to another embodiment of the present disclosure. As shown in FIG. 2F, housing 150 includes a recess 152 therein. Switch 252 is disposed within recess 152 to prevent a clinician from inadvertently adjusting the energy modality of the electrosurgical energy. A safety shield 254 may also be provided to cover switch 252. Thus, when a clinician wants to switch the energy modality, the clinician would have to open safety shield 254 before adjusting switch 252. Safety shield 254 may be opened by sliding or pivoting safety shield 254.

Figure 2G:
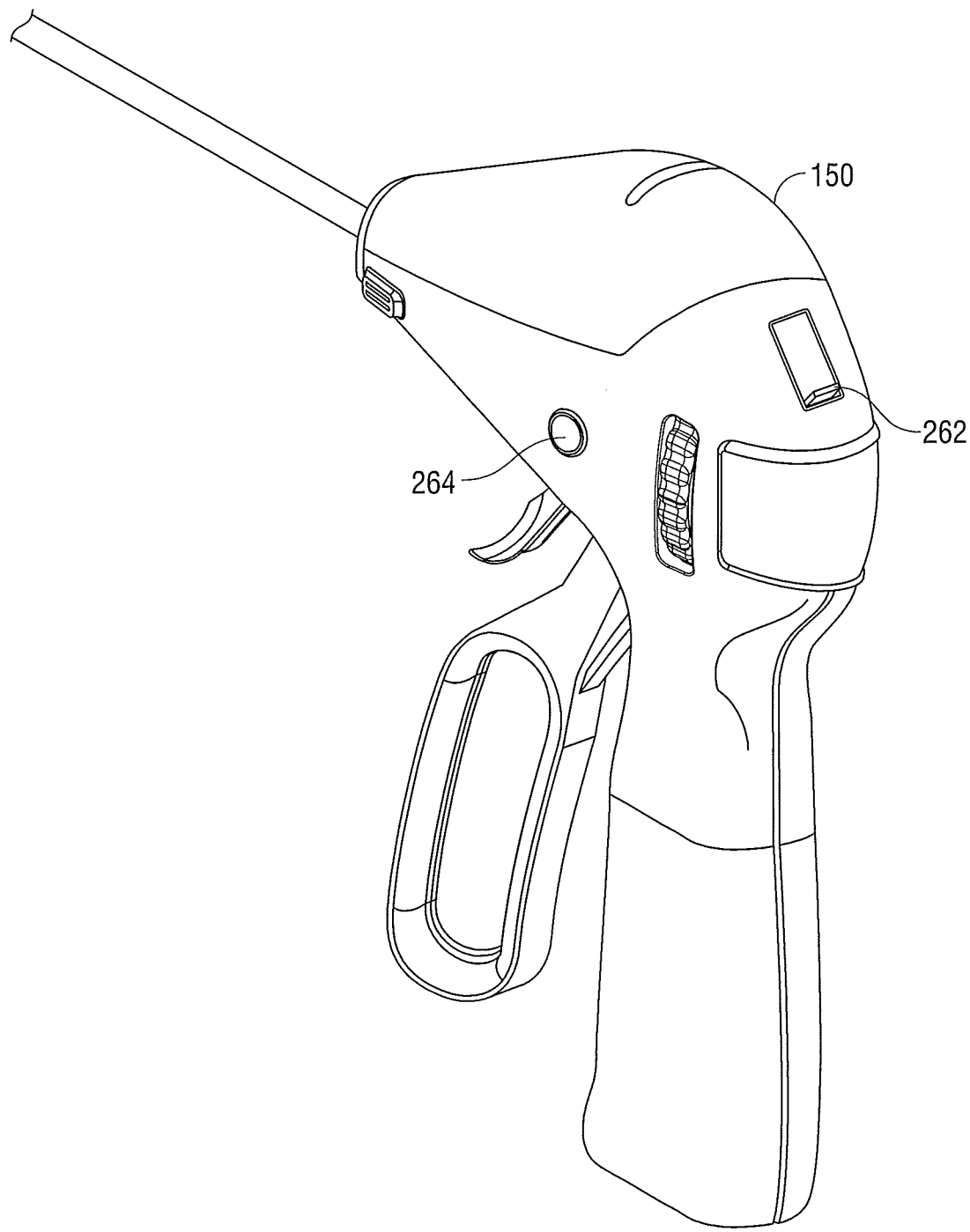

FIG. 2G depicts another safety device according to another embodiment of the present disclosure. As shown in FIG. 2G, a safety 264 is provided on housing 150. Safety 264 may be a mechanical switch (e.g., a slider or push button), a pair of electrical contacts, or a capacitance switch. In operation, a clinician is prevented from adjusting switch 262 unless the clinician de-activates safety 264 concurrently.

Figure 2H:
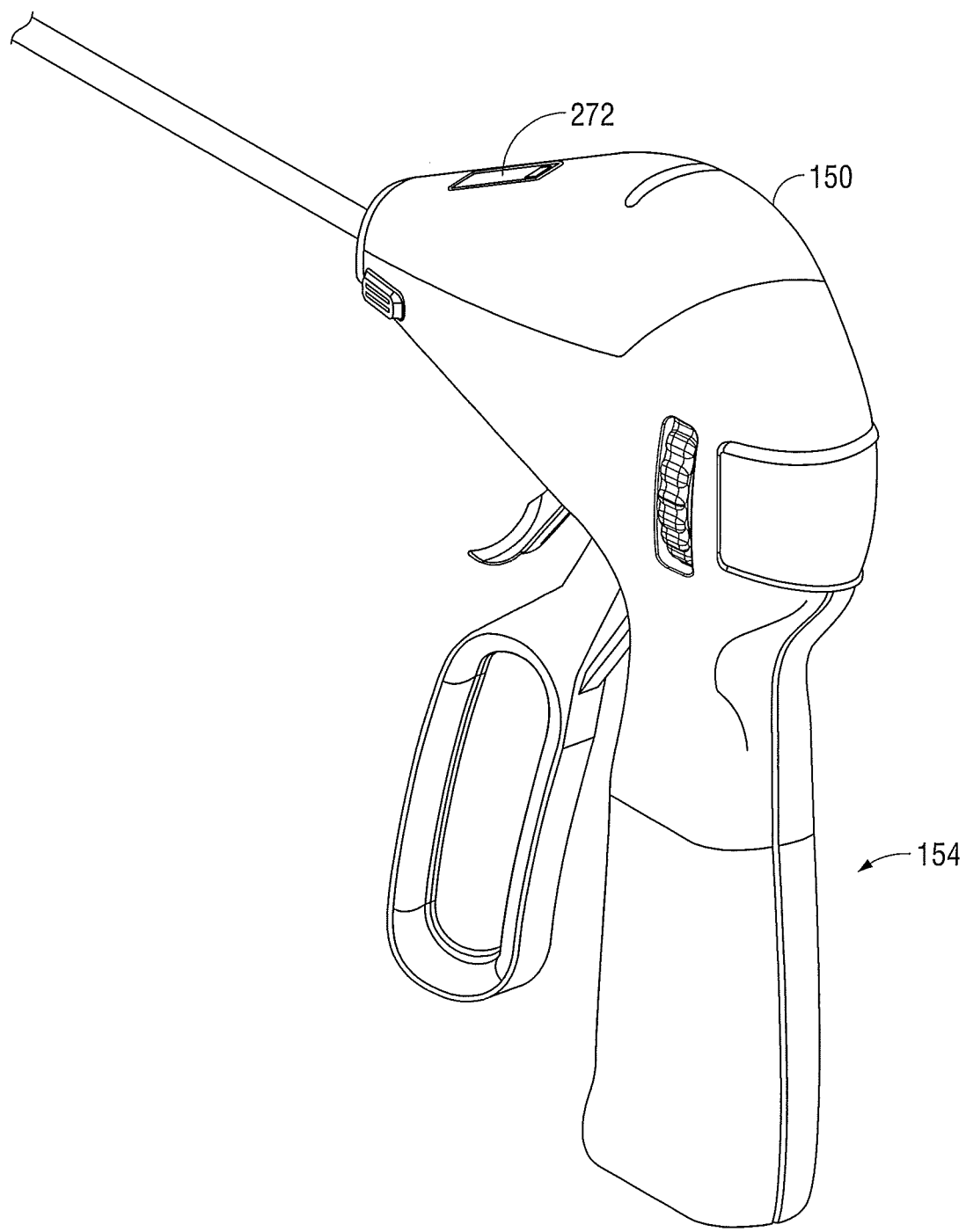
Figure 21:
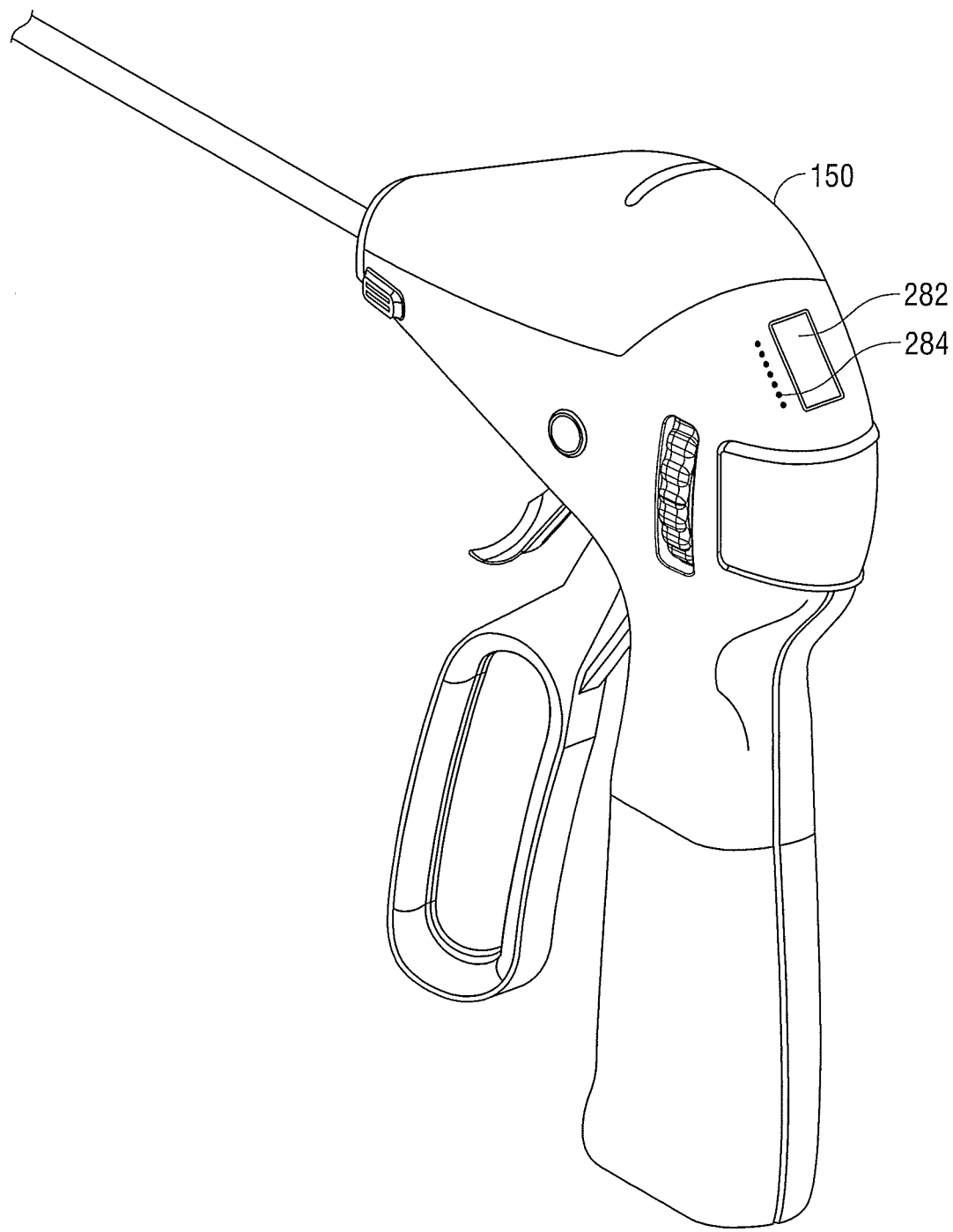

FIG. 2H depicts a method of preventing inadvertent adjustment of switch 272 according to another embodiment of the present disclosure. As shown in FIG. 2H, switch 272 is placed on top of housing 150 away from a handle 154. By placing switch 272 on top of housing 150, a clinician would have to use a different hand to adjust the energy modality or energy level. Any of the switches described above can be placed in the location of switch 272 shown in FIG. 2H.

FIG. 2I depicts a switch 282 according to another embodiment of the present disclosure. Switch 282 is a touch switch (e.g., a capacitance switch) that only needs to be touched in order to operate the switch. A clinician may slide his/her finger up and down the switch 282 to change the energy level or intensity. Alternatively, each successive tap of the touch switch 282 may adjust the energy modality or energy level. An indicator 284 may be provided to inform the clinician of the energy level or modality. Indicator 284 may include a number of LEDs or other visual indicators to indicate the energy level or modality.

Any of the switches described above may be permanently fixed to housing 150 or removable coupled to housing 150. Any of the switches may also be reposable or disposable.

Figure 3:
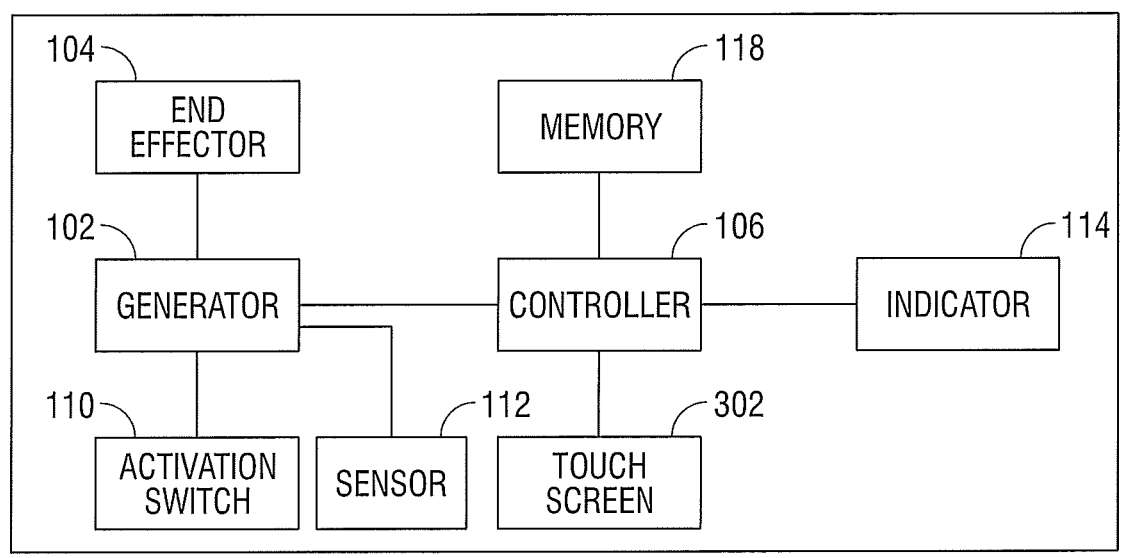
FIG. 3 is a system block diagram of an electrosurgical instrument according to another embodiment of the present disclosure.
Figure 4:
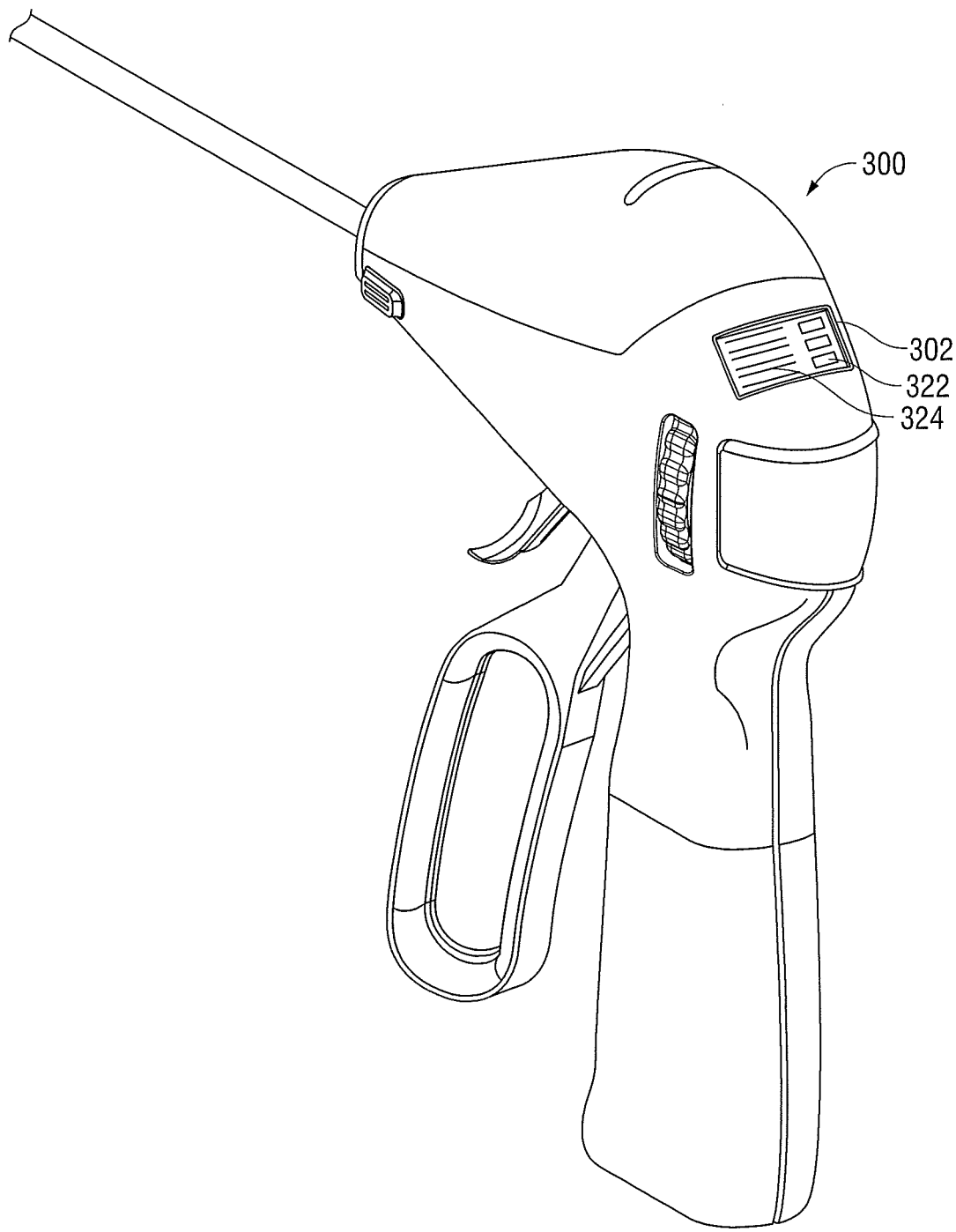
FIG. 4 is a perspective view of an electrosurgical instrument of the electrosurgical instrument of FIG. 3.

FIGS. 3 and 4 depict an electrosurgical instrument 300 according to another embodiment of the present disclosure. Electrosurgical instrument 300 includes a generator 102, end effector 104, activation button 110, sensors 112 controller 106, indicator 114, and memory 118 as described above with respect to FIG. 1. Further, instrument 300 also includes a touch screen 302 that controls electrosurgical instrument 300. Touch screen 302 may display various visual buttons 322 that allow a user to control the energy level and/or modality. Buttons 322 may cause instrument 300 to output energy having a selected energy level and/or modality. Alternatively, buttons 322 may open up a menu of options to select different energy levels and/or modalities. Buttons 322 may also be used to display information in display area 324 including, but not limited to, device information, energy output, sensor readings, duration of the electrosurgical procedure, waveform, energy level, energy modality.

Touch screen 302 may also be used to gather password information, clinician identification information, patient identification information, or biometric information to prevent unauthorized use of the instrument 300. Before, performing a procedure, a clinician may have to enter a password using a virtual keyboard displayed on touch screen 302. The virtual key board may display numeric characters such as 0-9, letters A-Z or a combination thereof. The virtual keyboard may also display a keypad similar to a telephone keypad that has letters corresponding to numbers.

The virtual keyboard may also be used to input a clinician identification information and/or patient identification information to keep records of the procedures performed on each patient by each clinician. Entering the clinician identification information and/or patient identification information may also call up specific programs or algorithms to be used during the electrosurgical procedure associated with the clinician and/or patient. The programs may be stored on memory 118 or they may be stored in a server (not shown) that communicates with electrosurgical instrument 300 via a standard network protocol. When the information is entered, touch screen 302 may display a list of patients to select from, a list of energy modalities to choose from, list of energy levels to use, or any other information that may be used during the electrosurgical procedure.

In another embodiment, touch screen 302 may be used to collect biometric information instead of entering clinician identification information and/or patient identification information. A clinician and/or patient can press one of his/her fingers on touch screen 302. Touch screen 302 captures an image of the fingerprint and compares it to a fingerprint stored in memory 118 or with a fingerprint stored in a server (not shown). If the image captured by touch screen 302 matches a stored fingerprint, the electrosurgical device is configured to be used as described above.

Figure 5:
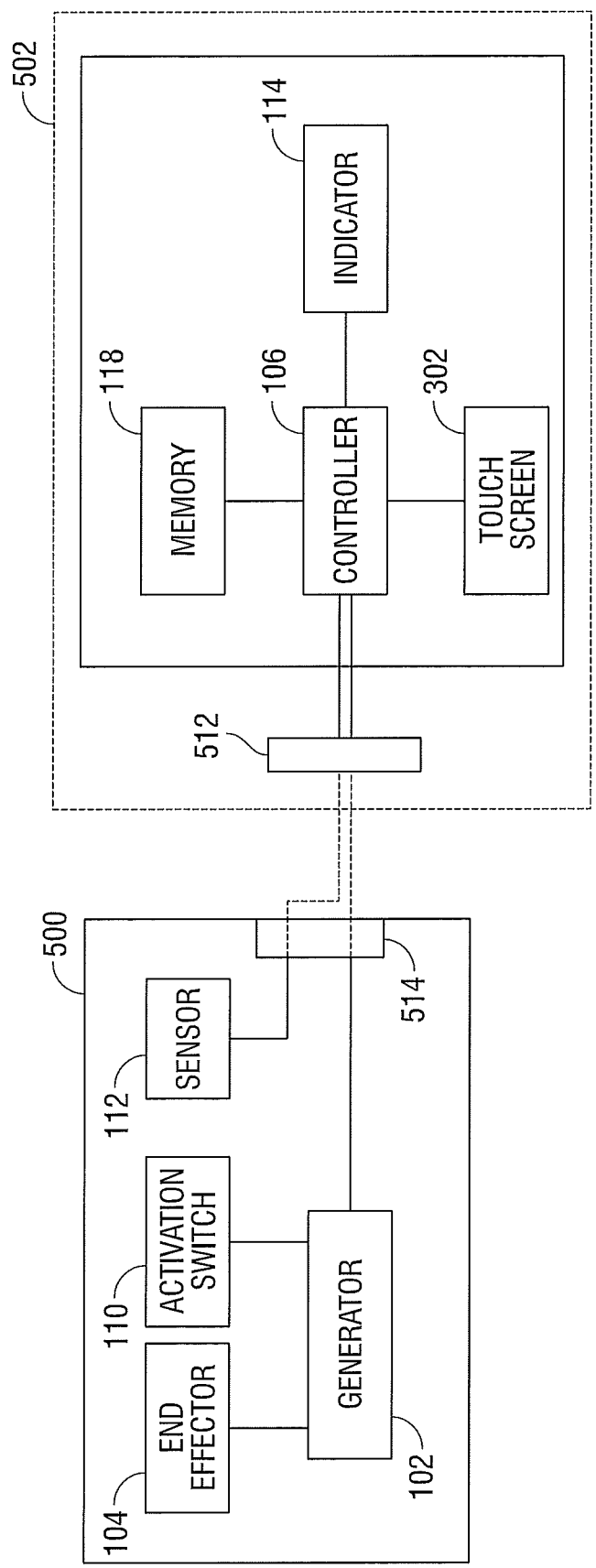
FIG. 5 is a system block diagram of an electrosurgical instrument according to another embodiment of the present disclosure.
Figure 6:
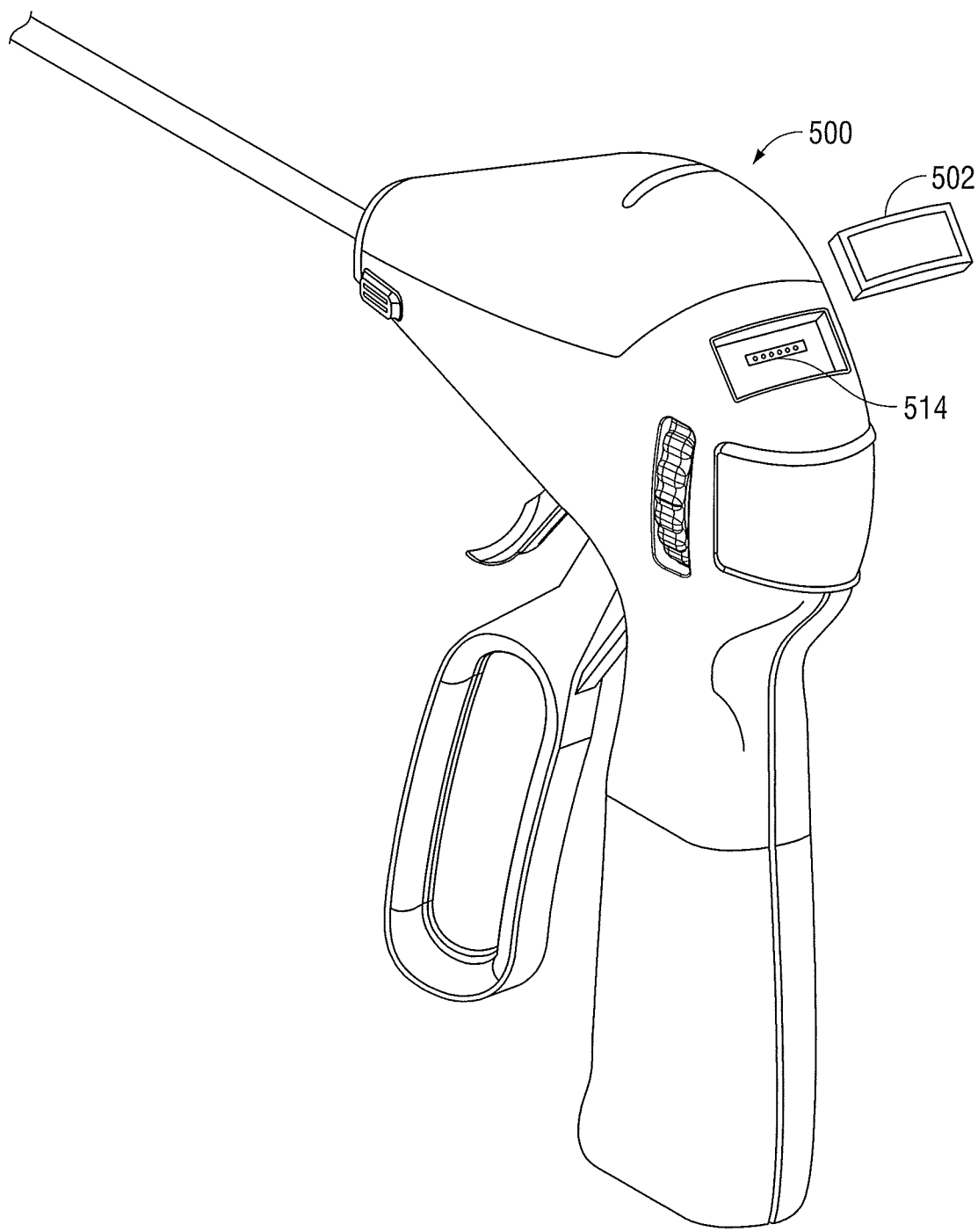
FIG. 6 is a perspective view of an electrosurgical instrument of the electrosurgical instrument of FIG. 5.

FIGS. 5 and 6 depict an alternative embodiment of the electrosurgical device shown in FIGS. 3 and 4. As shown in FIGS. 5 and 6, instrument 500 includes a generator 102, end effector 104, activation button 110, sensors 112, and interface 514. A control unit 502 is removable coupled to instrument 500. Control unit 502 may be disposable or reposable and includes a controller 106, indicator 114 (e.g., speaker), memory 118, and interface 512. When control unit 502 is coupled to instrument 500, interface 512 is coupled to interface 514. This allows control unit 502 to exercise control over the components of instrument 500 as well as allowing sensors 112 to send signals to controller 106.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. A handheld electrosurgical instrument, comprising:
   a housing including a generator configured to output electrosurgical energy;
   an elongated shaft directly coupled to the housing;
   an end effector disposed at a distal portion of the elongated shaft;
   a handle assembly coupled to the housing; and
   a control unit removably and directly coupled to the housing, the control unit including:
      a controller configured to control the output of the generator; and
      a touch screen configured to permit a user to select an energy modality of the electrosurgical energy and to provide a signal to the controller based on the selected energy modality.

2. The handheld electrosurgical instrument according to claim 1, wherein the energy modality includes an energy level and the touch screen provides an indication of the energy level.

3. The handheld electrosurgical instrument according to claim 1, wherein the energy modality includes an energy mode and the touch screen provides an indication of the energy mode.

4. The handheld electrosurgical instrument according to claim 1, wherein the energy modality includes an energy level and an energy mode and the touch screen provides an indication of the energy level and the energy mode.

5. The handheld electrosurgical instrument according to claim 1, wherein the touch screen is configured to receive clinician identification information and/or patient identification information.

6. The handheld electrosurgical instrument according to claim 5, where the touch screen displays information corresponding to the clinician identification information and/or the patient identification information.

7. The handheld electrosurgical instrument according to claim 1, wherein the touch screen is configured to receive biometric information.

8. The handheld electrosurgical instrument according to claim 7, further comprising a memory having biometric information stored thereon and the controller compares the received biometric information to the biometric information stored in a memory.

9. The handheld electrosurgical instrument according to claim 1, further comprising a memory having a plurality of energy modalities stored thereon.

10. The handheld electrosurgical instrument according to claim 1, further comprising an end effector operably coupled to the housing.

11. The handheld electrosurgical instrument according to claim 10, wherein the end effector is coupled to the generator and is configured to output electrosurgical energy to tissue.

\* \* \* \* \*